US007846460B2

(12) United States Patent
Chenevier et al.

(10) Patent No.: US 7,846,460 B2
(45) Date of Patent: Dec. 7, 2010

(54) COMPOSITION COMPRISING A MIXTURE OF ACTIVE PRINCIPLES, AND METHOD OF PREPARATION

(75) Inventors: Philippe Chenevier, Montreal (CA); Dominique Marechal, Laval (CA)

(73) Assignee: Ethypharm, Houdan (FR)

( * ) Notice: Subject to any disclaimer, the term of this patent is extended or adjusted under 35 U.S.C. 154(b) by 1187 days.

(21) Appl. No.: 10/544,311

(22) PCT Filed: Jan. 21, 2004

(86) PCT No.: PCT/EP2004/050035

§ 371 (c)(1), (2), (4) Date: Jan. 25, 2006

(87) PCT Pub. No.: WO2004/069135

PCT Pub. Date: Aug. 19, 2004

(65) Prior Publication Data

US 2006/0134422 A1    Jun. 22, 2006

Related U.S. Application Data

(60) Provisional application No. 60/447,198, filed on Feb. 13, 2003.

(30) Foreign Application Priority Data

Feb. 5, 2003  (FR) .................................. 03 01308

(51) Int. Cl.
*A61K 9/14* (2006.01)
*A61K 9/16* (2006.01)
*A61K 9/20* (2006.01)
(52) U.S. Cl. ....................................... 424/401; 424/400
(58) Field of Classification Search ...................... None
See application file for complete search history.

(56) References Cited

U.S. PATENT DOCUMENTS 7,332,183 B2 *  2/2008  Plachetka et al. ........... 424/472

FOREIGN PATENT DOCUMENTS

| EP | 1 020 182 A2 | 7/2000 |
|---|---|---|
| JP | 2000 044404 A | 2/2000 |
| WO | WO 02/11702 A2 | 2/2002 |
| WO | WO 02/39981 A1 | 5/2002 |
| WO | WO 03/005993 A1 | 1/2003 |

* cited by examiner

*Primary Examiner*—Robert A Wax
*Assistant Examiner*—Melissa S Mercier
(74) *Attorney, Agent, or Firm*—Heslin Rothenberg Farley & Mesiti PC

(57) ABSTRACT

Active principle-based coated particle, in which both the core and the coating contain active principle, includes a core which contains a first active principle while the coating contains a second active principle, which is different in nature.

20 Claims, No Drawings

COMPOSITION COMPRISING A MIXTURE OF ACTIVE PRINCIPLES, AND METHOD OF PREPARATION

CROSS REFERENCE TO RELATED APPLICATIONS

This application is a 371 filing of PCT International application no. PCT/EP2004/050035 filed on Jan. 21, 2004 and published in English as WO 2004/069135 A2 on Aug. 19, 2004 which claims priority of French application no. 03.01308 filed Feb. 5, 2003 and U.S. provisional application Ser. No. 60/447,198 filed Feb. 13, 2003, the disclosures of which are hereby incorporated by reference in their entirety.

The present invention relates to coated particles comprising two active principles, to the method of preparation thereof and to the multiparticulate tablets comprising said particles.

Pharmaceutical forms comprising two active principles already exist, in unit forms such as gelatin capsules or tablets.

In these pharmaceutical forms, a first alternative consists in formulating each active principle individually.

The two populations are then either compressed without a prior mixing step, in the form of bilayer tablets, technically complex to set up and requiring a specific material for the compression, or mixed, before being compressed, placed in gelatin capsules or in sachets.

A second alternative consists in simultaneously formulating the two active principles, for example by mixing, followed by a granulation step, the resulting product possibly then being compressed, placed in gelatin capsules or in sachets.

These mixtures are often complicated to control since they bring together several populations of active principles and of excipients of heterogeneous respective size, mass and form. There ensues therefrom an increased risk of segregation, leading to a gradual demixing of the two populations of active particles during the mixing itself or the pharmaceutical operations following the mixing, for example the compression or the placing in gelatin capsules. The final unit form contains a highly variable content of each of the two active principles.

Choosing the populations of active principles and of excipients needs great care but is not, however, sufficient to completely eliminate this risk.

In the case of a mixture of active principles, the risk of segregation, already high due to the presence of an additional population, becomes even more unfavorable when the dose ratio between the active principle present at the highest dose and that present at the lowest dose is high, in particular when it becomes equal to or greater than 5, preferably equal to or greater than 10.

To compensate for this unfavorable dose ratio and to maintain a ratio of the respective masses of each fraction close to 1, a diluent is usually added to the fraction present at the lowest dose with which said active principle is granulated.

The addition of the diluent to the particle formulation leads to an increase in the unit size and weight of the pharmaceutical form to be administered to the patient, which creates an additional obstacle to be overcome in formulating the medicinal product, and makes it more difficult to administer to patients who have difficulty in swallowing.

A second problem appears in the case of combinations of active principles in which at least one of the active principles, or even both, require(s) a coating to mask its (their) unpleasant taste.

In this case, the size of the particles is increased by the polymeric coating layer masking the taste.

It would therefore be advantageous to have a composition which is such that the risks of heterogeneity in terms of mass and of size and, where appropriate, of content, set out above, would be avoided, and which is suitable for any subsequent formulating, for example compression, placing in gelatin capsules or coating.

To solve this problem, the Applicant has developed coated particles combining two active principles different in nature, respectively a first active principle which is a constituent of all or part of the core and a second active principle which is a constituent of all or part of the coating.

In the remainder of the description, the expression "coating" denotes a coating comprising at least one coating layer. Should the coating consist of several layers, each layer would have the same composition, applied in practice by spraying onto the core. However, it should be noted that, since one of the aims is to obtain coated particles as small as possible in size, the particle will advantageously be coated with a single layer. The coating applied around the core is to be distinguished from the additional functional layer to which reference will subsequently be made, and which denotes an additional layer applied to the basic coating.

In other words, and according to the invention, the same particle combines two different active principles making it possible to solve the problems mentioned above relating to the population heterogeneity of the particles used, in terms of size and shape.

The invention therefore relates to an active principle-based coated particle in which both the core and the coating contain active principle, wherein the core contains a first active principle while the coating contains a second active principle, which is different in nature.

The Applicant has presented, in patent application WO 02/39981, a substantially spherical microgranule consisting of a core coated with at least one coating layer, the core and said coating layer each containing between 80 and 95% by weight of active principle, the rest up to 100% consisting of at least one binding agent. According to that document, the active principle constituting the core is the same as that contained in the coating layer. In addition, the set of examples describes only embodiments based on a single active principle.

To solve the problem of the heterogeneity of content of active principle in cases, therefore, where the two active principles have a different concentration in the coated particle, the core contains the active principle present at the highest dose, while the coating contains the active principle present at the lowest dose.

In an advantageous embodiment, the dose ratio between the active principle present at the highest dose (first active principle) and that present at the lowest dose (second active principle) is equal to or greater than 5, preferably equal to or greater than 10.

The coated particle comprises two active principles which can be chosen from any family of compounds, for example from gastrointestinal sedatives, antacids, analgesics, anti-inflammatories, coronary vasodilators, peripheral and cerebral vasodilators, anti-infectious agents, antibiotics, antiviral agents, antiparasitic agents, anticancer agents, anxiolytics, neuroleptics, central nervous system stimulants, antidepressants, antihistamines, antidiarrheal agents, laxatives, nutrient supplements, immunosuppressants, blood cholesterol-reducing agents, hormones, enzymes, antispasmodics, anti-angina agents, medicinal products affecting cardiac rhythm, medicinal products used in the treatment of arterial hypertension, antimigraine agents, medicinal products affecting blood coagulability, antiepileptics, muscle relaxants, medicinal products used in the treatment of diabetes, medicinal products used in the treatment of thyroid dysfunctions, diuretics, anorectic agents, anti-asthmatics, expectorants, antitussives, mucoregulators, decongestants, hypnotics, antinausea agents, hematopoietic agents, uricosuric agents, plant extracts and contrast agents, or any other family of compounds, the active principles combined in the tablet possibly being chosen from the same family or from different families.

Combinations, which concern medicinal products of the same family or of different families, are particularly studied by the pharmaceutical industry for treating serious pathological conditions requiring the prescription of several specialty products in conjunction, since they make it possible to improve adherence to treatments by decreasing the number of units to be taken by the patient, and sometimes make it possible to obtain a synergy of effects.

Combinations of active principles are of particular use in the field of analgesia, when a synergistic effect on the treatment of pain is sought by combining two reasonably powerful analgesics, such as, for example, oxycodone and paracetamol, hydrocodone and paracetamol, paracetamol and tramadol, or combinations combining an opioid analgesic, for example oxycodone, with an opioid receptor antagonist, such as naloxone or naltrexone, so as to avoid incorrect use of medicinal products by drug addicts.

In the field of antiulcer agents, preferred combinations combine an antacid with an antiulcer agent, for example antacids and omeprazole or lansoprazole, antacids and famotidine or ranitidine.

In the field of blood cholesterol-reducing agents and antidiabetic agents, preferred combinations combine fenofibrate with metformin or fenofibrate with simvastatin.

Other domains are particularly studied, such as those of medicinal products effective against the AIDS virus or anticancer agents.

According to the invention, the composition of the coated particles will vary as a function of the size of the particles of the active principles used and of the content of each active principle in the final coated particle.

In a first embodiment, the core contains 100% by weight of the first active principle, while the coating contains from 60 to 99% by weight of the second active principle, advantageously from 80 to 99% by weight, the rest up to 100% consisting of at least one binding agent and optionally an antistatic agent.

In this first embodiment, the rest up to 100% of the coating can also consist exclusively of binding agent.

In a second embodiment, the core contains from 60 to 99% by weight of the first active principle, advantageously from 80 to 99% by weight, while the coating contains from 60 to 99% by weight of the second active principle, advantageously from 80 to 95% by weight, the rest up to 100% of the core and of the coating consisting of at least one binding agent and optionally an antistatic agent.

In this second embodiment, the rest up to 100% by weight of the core and of the coating can consist exclusively of a binding agent, which may be identical or different.

As already mentioned, in all cases, the addition of an antistatic agent to the suspension or the solution used for the coating may be envisaged.

The choice of the binding agent will be determined as a function not only of its ability to bind the particles of active principle to one another within the coated core, but also of the functional characteristics of the desired coated core, whether in the presence or absence of subsequent functional coating. The expression "functional characteristic" denotes in particular, but in a nonlimiting manner, the properties of taste masking and of modified or unmodified release of the active principle.

In practice, the binding agent is chosen from the group comprising in particular cellulosic polymers, acrylic polymers, povidones, copovidones, polyvinyl alcohols, alginic acid, sodium alginate, starch, pregelatinized starch, sucroses and derivatives thereof, guar gum, polyethylene glycols, and mixtures thereof.

At the time of production of the core or of the coating, the binding agent is sprayed in a solvent chosen from the group comprising water and organic solvents, such as ethanol, isopropanol or acetone, alone or as a mixture.

As already mentioned, the core and the coating comprise an antistatic agent which is present, in principle, in proportions possibly ranging up to 10% by weight, preferably up to 3% by weight, relative to the weight of the core and up to 10% by weight, preferably up to 3% by weight, relative to the weight of the coating, and which can be chosen from the group comprising micronized or nonmicronized talc, colloidal silica (Aerosil®200), treated silica (Aerosil®R972) or precipitated silica (Syloid®FP244), and mixtures thereof.

By virtue of their structure consisting of a core which is itself coated with a layer which gives it a substantially spherical shape, the particles of the invention may advantageously then be coated with an additional functional layer, the composition of which is chosen as a function of the desired characteristics of taste masking and/or of release of the active principles.

The composition of the additional functional layer is chosen as a function of the physicochemical characteristics of each active principle, and consists of at least one coating polymer.

The coating polymer is advantageously chosen from the group comprising cellulosic polymers, acrylic polymers and mixtures thereof.

Among cellulosic polymers, ethylcellulose, hydroxypropylcellulose (HPC) and hydroxypropylmethylcellulose (HPMC), alone or as a mixture, will advantageously be chosen.

Among acrylic polymers, ammonio methacrylate copolymer (Eudragit® RL and RS), polyacrylate (Eudragit® NE) and polymethacrylate (Eudragit® E) will advantageously be chosen, Eudragit® being a trademark registered by RÖHM.

The additional functional layer is applied by spraying a solution, or a suspension, or else a colloidal dispersion, of the coating polymer in a solvent or a mixture of solvents, so as to form a continuous film covering the entire surface of each particle, whatever its surface finish, in an amount sufficient to obtain, for example, a masking of taste which is effective at the time the medicinal product is taken and throughout the time the coated particles remain in the buccal cavity.

The thickness of the film, which is generally between 5 and 75 µm, most commonly depends on the solubility of the active principle contained in the coating (second active principle) at the pH of saliva and on the more or less pronounced nature of the bitterness thereof.

The polymer of the additional functional layer is applied to the surface of the coated particles of the invention in proportions possibly ranging up to 40%, preferably up to 20%, calculated as weight gain relative to the mass to be coated.

The solvent chosen for spraying the coating polymer contained in the additional functional layer may be water, an organic solvent, such as ethanol, isopropanol or acetone, or a mixture of solvents.

The additional functional layer also optionally comprises a plasticizer, a surfactant, an antistatic agent, a lubricant.

The plasticizer is used in a proportion of at most 40%, preferably between 15 and 30%, expressed by weight relative to the dry weight of polymer, and chosen from the group comprising triethyl citrate, acetyltributyl citrate, triacetine, tributyl citrate, diethyl phthalate, polyethylene glycols, polysorbates, mono- and diacetylated glycerides, and mixtures thereof.

The surfactant is chosen from anionic, cationic, nonionic and amphoteric surfactants.

The antistatic agent is used in a proportion of at most 10% by weight, preferably between 0 and 3%, preferably less than 1%, by weight, calculated relative to the dry weight of the polymer, and chosen from the group comprising micronized or nonmicronized talc, colloidal silica (Aerosil®200), treated silica (Aerosil®R972) or precipitated silica (Syloid®FP244), and mixtures thereof.

The lubricant is used in a proportion of at most 10% by weight, preferably between 0 and 3%, preferably less than 1%, by weight, calculated relative to the dry weight of the polymer and is chosen from the group comprising magnesium stearate, stearic acid, sodium stearyl fumarate, poly (oxyethylene glycols), sodium benzoate and mixtures thereof.

The size of the coated particles is conventionally between 50 µm and 2 mm, preferably between 100 and 800 µm, even more preferably between 200 and 500 µm, and is determined by conventional methods, for example using a set of sieves of calibrated mesh size, or by laser diffraction.

A subject of the present invention is also a pharmaceutical or cosmetic composition containing said coated particles.

The coated particles, possibly covered with an additional functional layer, may be used in any type of formulation intended for oral administration, but are particularly suitable when the pharmaceutical form chosen involves bringing the coated particles into contact with saliva.

Particularly preferred pharmaceutical forms are powders intended for oral administration, packaged in the form of sachets, or of drinkable suspensions in liquid form or to be reconstituted by extemporaneous addition of a certain volume of water, or else tablets, in particular multiparticulate tablets which are orodispersible or dispersible in a small volume of water. Orodispersible tablets define tablets intended to disintegrate or to solubilize in the mouth without chewing, upon contact with saliva, in less than 60 seconds, preferably less than 40 seconds, forming a suspension of particles, which may or may not be coated, which is easy to swallow.

The disintegration time corresponds to the amount of time between the moment at which the tablet is placed in the mouth in contact with saliva and the moment at which the suspension resulting from the disintegration or the dissolving without chewing of the tablet in contact with saliva is swallowed.

This type of tablet is, for example, described in documents EP 548356, EP 636364, EP 1003484, EP 1058538, WO 98/46215, WO 00/06126, WO 00/27357 and WO 00/51568, but the particle of the invention can also be used in any other formulation equivalent to those described in the documents mentioned.

Initially, the coated particles are released into the buccal cavity after the tablet has disintegrated or dissolved by the action of the saliva, then they release the active principle rapidly in the gastrointestinal tract, in the stomach or in the duodenum.

The orodispersible tablet consists of the particles of the invention and of a mixture of excipients comprising at least one disintegration agent, a soluble diluent, a lubricant and, optionally, a swelling agent, a permeabilizing agent, sweeteners and flavorings.

The proportion of excipient mixture relative to the coated particles is conventionally between 0.4 and 10, preferably between 1 and 5, parts by weight.

The disintegration agent is chosen from the group comprising in particular crosslinked sodium carboxy-methylcellulose denoted in the trade by the term croscarmellose, crospovidone and mixtures thereof.

The disintegration agent is used in a proportion of between 1 and 20% by weight, preferably between 5 and 15% by weight, in the case of a mixture, each disintegrating agent being between 0.5 and 15% by weight, preferably between 5 and 10%, by weight, calculated relative to the weight of the tablet.

The diluent may be chosen from the group comprising in particular soluble agents with binding properties, preferentially polyols of less than 13 carbon atoms, lactose, cellulose derivatives and preferentially microcrystalline cellulose.

The preferred polyol of less than 13 carbon atoms is chosen from mannitol, xylitol, sorbitol and maltitol.

The diluent is used in a proportion of between 20 and 90% by weight, preferably between 30 and 50% by weight, calculated relative to the weight of the tablet.

The soluble diluent is in the form of a directly compressible product the mean diameter of the particles of which is from 100 to 500 µm, or in the form of a powder the mean diameter of the particles of which is less than 100 µm, said powder being used alone or as a mixture with the directly compressible product.

In a preferred embodiment, the polyol is used in the form of the directly compressible product.

In a second preferred embodiment, a directly compressible polyol and a polyol in the form of a powder are mixed, the polyol in this case being identical or different, the respective proportions of directly compressible polyol and of powdered polyol being from 99/1 to 20/80, preferably from 80/20 to 20/80.

The lubricant is chosen from the group comprising magnesium stearate, stearic acid, sodium stearyl fumarate, poly (oxyethylene glycols), sodium benzoate and mixtures thereof.

The lubricant is used in a proportion between 0.02 and 2% by weight, preferably between 0.5 and 1% by weight, calculated relative to the weight of the tablet.

The lubricant is dispersed in the mixture of compression excipients sprayed at the surface of the tablet at the time of compression, completely or partially.

The swelling agent is chosen from the group comprising microcrystalline cellulose, starches and modified starches.

The swelling agent is used in a proportion of between 1.0 and 15% by weight, calculated relative to the weight of the tablet.

The permeabilizing agent is chosen from the group comprising in particular silicas having great affinity for aqueous solvents, such as precipitated silica, more well-known under the trademark Syloid®, maltodextrins, β-cyclodextrins and mixtures thereof.

The permeabilizing agent is used in a proportion of between 0.5 and 5.0% by weight, calculated relative to the weight of the tablet.

The antistatic agent may be chosen from the group comprising micronized or nonmicronized talc, colloidal silica (Aerosil®200), treated silica (Aerosil®R972) or precipitated silica (Syloid® FP244), and mixtures thereof.

The antistatic agent is used in a proportion of between 0.5 and 5.0% by weight, calculated relative to the weight of the tablet.

The sweetener may be chosen from the group comprising in particular aspartame, potassium acesulfame, sodium saccharinate, neohesperidine dihydrochalcone, sucralose, monoammonium glycyrrhizinate, and mixtures thereof.

The flavorings and dyes are those conventionally used in pharmacy for preparing tablets.

The invention also relates to the method for preparing the coated particles described above.

The method in accordance with the invention comprises the following steps:
  preparing a core comprising the first active principle,
  coating the core thus obtained by spraying a solution or suspension comprising the second active principle and at least one binding agent,
  drying.

In a first preferred embodiment, the particles are prepared according to the following steps:
  granulation of the first active principle in the form of a powder, using a binding agent in the form of an aqueous or organic solution or a solvent mixture, and then drying,
  coating of the core thus obtained by spraying the solution or the suspension comprising the second active principle and at least one binding agent,
  drying.

In a second preferred embodiment, the particles are prepared according to the following steps:
  granulometric selection of microcrystals of between 50 µm and 400 µm in size constituting the first active principle,
  coating of the microcrystals by spraying the solution or the suspension comprising the second active principle and at least one binding agent,
  drying.

According to this embodiment, the steps may be carried out in different devices or in the same device.

For the granulation, a high energy granulator, a planetary mixer or a fluidized air bed are advantageously used.

In the case of granulation in a fluidized air bed, the mixture of powder containing the active principle, and optionally the diluent and the antistatic agent, is introduced into the device, before being granulated, by spraying onto said mixture of powder a solution or suspension of excipients comprising at least one binding agent.

When the two active principles are incompatible with one another, such that accelerated degradation of one of them is observed, it is possible to apply, between the core comprising the first active principle and the coating comprising the second active principle, an optional polymer layer separating the two active principles. Said layer then consists of a polymer which can be used as a binding agent, ideally the same polymer as that used as binding agent in one or other of the steps for preparing the particle, the amount of polymer applied not exceeding 15%, preferably not exceeding 5%, calculated as weight gain relative to the mass to be coated.

If the organoleptic characteristics of the particle make it necessary, an additional step of coating the coated cores thus obtained is carried out by spraying an additional functional layer which masks the taste, followed by drying.

All the steps of the method in accordance with the invention can be carried out in a sugar-coating pan or a perforated pan or in a fluidized air bed.

In a preferred embodiment of the method in accordance with the invention, all the steps for preparing the coated core and for coating with the additional layer are carried out in a fluidized air bed.

The fluidized air bed is equipped with a spray nozzle, the spray direction and position of which can be chosen.

This choice makes it possible to control the kinetics of growth of the particles and to avoid phenomena of sticking, related to the nature of the active principle, to the composition of the sprayed binding or coating composition, and to the various parameters of the method (temperature, air pressure for example, solution flow rate).

According to an advantageous embodiment, the binding agent used to prepare the particle and the polymer used to mask the taste of said particle are identical.

The invention also relates to the method for preparing the multiparticulate tablets comprising the coated particles.

The method in accordance with the invention comprises the following steps:
  dry mixing of the particles, obtained according to the method described above, with the compression excipients,
  compressing of the mixture to obtain a unit form.

The compression of the mixture may be carried out on an alternating or rotary compression machine.

The constraints exerted during the compression step may range from 5 kN to 50 kN, preferably from 5 kN to 15 kN.

The hardness of these tablets is preferably between 1 and 10 kp, more preferentially between 1 and 5 kp, measured according to the method of the European Pharmacopoeia (2.9.8), 1 kp being equal to 9.8 N.

Preferably, the hardness of the multiparticulate tablet is suitable for obtaining a friability, measured according to the method of the European Pharmacopoeia, of less than 2%, while at the same time conserving a dissolution profile identical to that of the coated particles alone and for the multiparticulate tablets, and permitting a disintegration time for the tablet in the mouth of less than or equal to 60 seconds, preferably less than or equal to 40 seconds.

The tablets may have a diameter of between 6 mm and 17 mm. They may be round, oval or oblong in shape, have a flat or concave surface, and optionally have grooves.

In the case of orodispersible tablets, "polo"-shaped punches may also be used.

The tablets have a mass of between 0.1 gram and 2.0 grams.

The invention will be understood more clearly by means of the examples of preparation of the coated particles and of the multiparticulate tablets in accordance with the invention. These examples are given only by way of illustrations and of advantageous embodiments of the invention and in no way constitute a limitation thereof.

Materials and Analytical Methods

Excipients Used
  mannitol: Pearlitol®200SD marketed by ROQUETTE.
  microcrystalline cellulose: Avidel® PH102 marketed by FMC
  colloidal silica: Syloid® 244FP marketed by BASF
  HPMC: Pharmacoat® 603 marketed by SHIN-ETSU methacrylate copolymer: Eudragit®E100 marketed by RÖHM
  aspartame: marketed by Nutrasweet.
  Method for dissolving pH 1.2
  device: USP type II
  blade speed: 50 rpm
  volume: 900 ml
  temperature: 37.0° C.±0.5° C.
  detection: UV spectrophotometry at 210 nm for hydrocodone bitartrate, 280 nm for oxycodone hydrochloride, 298 nm for paracetamol.
  dissolving medium: 0.1N HCl

EXAMPLE 1

Coated Particles Combining Oxycodone Hydrochloride and Paracetamol

An aqueous solution containing 30.8 grams of oxycodone HCl ("oxycodone") and 8.0 grams of hydroxypropylmethylcellulose ("HPMC") as binding agent (25% by weight relative to oxycodone) is sprayed onto 1000 grams of paracetamol crystals having a mean size of 350 μm, in a fluidized air bed of the GPCG-3 type, equipped with a Würster nozzle ("bottom spray").

1038 grams of the particles obtained after the assembly step described above are coated, in a GLATT GPCG-3 fluidized air bed equipped with a Würster insert, by spraying an alcohol solution of Eudragit®E100, comprising 10% by weight of colloidal silica, calculated relative to the dry weight of polymer.

A total amount of Eudragit®E100 corresponding to 20% calculated in weight gain relative to the starting particle mass is applied to the particles.

The final formulation of the coated particles appears in table 1:

TABLE 1

|  | % (w/w) |
| --- | --- |
| paracetamol | 78.9 |
| oxycodone hydrochloride | 2.4 |
| HPMC | 0.6 |
| Eudragit E100 | 16.5 |
| colloidal silica | 1.6 |
| denatured alcohol | n/a |
| USP purified water | n/a |
| TOTAL | 100 |

EXAMPLE 2

Orodispersible Tablets Containing 325 mg of Paracetamrol and 10 mg of Oxycodone Hydrochloride The coated particles obtained in Example 1 are mixed with excipients, according to table 2, the mixture thus obtained is then compressed on an SVIAC PR6 press equipped with 6 round, flat punches 15 mm in diameter, so as to obtain an average unit dose of 325 mg of paracetamol and 10 mg of oxycodone.

The final formulation of the tablets thus obtained appears in table 2:

TABLE 2

|  | % (w/w) | mg/tablet |
| --- | --- | --- |
| coated particles | 42.6 | 447.61 |
| mannitol | 33.0 | 346.1 |
| Crospovidone CL | 10.0 | 105.0 |
| microcrystalline cellulose | 10.0 | 105.0 |
| aspartame | 2.0 | 21.0 |
| mint flavoring | 0.5 | 5.25 |
| colloidal silica | 0.5 | 5.25 |
| magnesium stearate | 1.25 | 13.13 |
| TOTAL | 100 | 1050 |

These tablets have the following characteristics (table 3):

TABLE 3

| weight (mg) | 1050 |
| --- | --- |
| hardness (kP) | 3.5 |
| friability (%) | 0.6 |
| disintegration in the mouth (s) | 25 |

A dissolution test in medium with a pH of 1.2 is carried out according to the method previously described, in order to determine the in vitro release kinetics of each of the two active principles (table 4):

TABLE 4

| Time (minutes) | % (w/w) paracetamol released | % (w/w) oxycodone HCl released |
| --- | --- | --- |
| 2.5 | 45 | 80 |
| 15 | 100 | 100 |
| 30 | 100 | 100 |
| 60 | 100 | 100 |

EXAMPLE 3

Coated Particles Combining Hydrocodone Bitartrate and Paracetamol

An aqueous solution containing 30.8 grams of hydrocodone bitartrate ("hydrocodone") and 9.2 grams of hydroxypropylmethylcellulose ("HPMC") as binder (30% by weight relative to hydrocodone) is sprayed onto 1000 grams of paracetamol crystals having a mean size of 350 μm, in a fluidized air bed of the GPCG-3 type, equipped with a Würster nozzle ("bottom spray").

1039 grams of the particles obtained after the assembly step described above are coated, in a GLATT GPCG-3 fluidized air bed equipped with a Würster insert, by spraying an alcoholic solution of Eudragit®E100, comprising 10% by weight of colloidal silica, calculated relative to the dry weight of polymer.

A total amount of Eudragit®E100 corresponding to 20% calculated as weight gain relative to the starting particle mass is applied to the particles.

The final formulation of the coated particles appears in table 5:

TABLE 5

|  | % (w/w) |
| --- | --- |
| paracetamol | 79.5 |
| hydrocodone bitartrate | 2.5 |
| HPMC | 0.7 |
| Eudragit E100 | 15.7 |
| colloidal silica | 1.6 |
| denatured alcohol | n/a |
| USP purified water | n/a |
| TOTAL | 100 |

EXAMPLE 4

Orodispersible Tablets Containing 325 mg of Paracetamol and 10 mg of Hydrocodone Bitartrate The coated particles obtained in Example 3 are mixed with excipients according to table 5, the mixture thus obtained is then compressed on an SVIAC PR6 press equipped with 6 round, flat punches 15 mm in diameter, so as to obtain a mean unit dose of 325 mg of paracetamol and 10 mg of hydrocodone.

The final formulation of the tablets thus obtained appears in table 6:

TABLE 6

|  | % (w/w) | mg/tablet |
|---|---|---|
| coated particles | 30.6 | 428.0 |
| mannitol | 55.7 | 780.0 |
| Crospovidone CL | 10.0 | 140.0 |
| aspartame | 2.0 | 28.0 |
| mint flavoring | 0.2 | 3.5 |
| colloidal silica | 0.5 | 7.0 |
| magnesium stearate | 1.0 | 14.0 |
| TOTAL | 100 | 1400 |

These tablets have the following characteristics (table 7):

TABLE 7

| weight (mg) | 1400 |
|---|---|
| hardness (kP) | 4.0 |
| friability (%) | 0.4 |
| disintegration in the mouth (s) | 30 |

A dissolution test in medium with a pH of 1.2 is carried out according to the method previously described, in order to determine the in vitro release kinetics of each of the two active principles (table 8):

TABLE 8

| Time (minutes) | % (w/w) paracetamol released | % (w/w) hydrocodone bitartrate released |
|---|---|---|
| 2.5 | 35 | 80 |
| 15 | 75 | 100 |
| 30 | 90 | 100 |
| 60 | 100 | 100 |

The invention claimed is:

1. An active principle-based coated particle having a size between 50 µm and 2 mm and comprising a core and a coating, each of which contains an active principle, wherein the core consists of a first active principle, and the coating consists of from 60 to 99% by weight of a second active principle that is different in nature from the first active principle, the rest up to 100% by weight of the coating consisting of at least one binding agent.

2. The coated particle as claimed in claim 1, wherein the first active principle and the second active principle have a different concentration in the coated particle, and the first active principle in the core has a higher dose amount than the second active principle in the coating.

3. The coated particle as claimed in claim 2, wherein a dose ratio between the first active principle and the second active principle is equal to or greater than 5.

4. The coated particle as claimed in claim 1, wherein the rest up to 100% of the coating consists exclusively of a binding agent.

5. The particle as recited in claim 1, wherein the at least one binding agent is selected from the group consisting of cellulosic polymers, acrylic polymers, povidones, copovidones, polyvinyl alcohols, alginic acids, sodium alginate, starch, pregelatinized starch, sucroses and derivatives thereof, guar gym, and polyethylene glycols, alone or as mixtures thereof.

6. An active principle-based coated particle having a size between 50 µm and 2 mm and comprising a core and a coating, each of which contains an active principle, wherein the core consists of a first active principle, and the coating consists of from 60 to 99% by weight of a second active principle that is different in nature from the first active principle, the rest up to 100% by weight of the coating consisting of at least one binding agent and at least one antistatic agent in proportions ranging respectively up to 10% by weight, relative to the weight of the coating.

7. The coated particle as claimed in claim 1, which comprises, in addition to the coating, an additional functional layer, composition of which is chosen as a function of desired characteristics of taste masking and/or of release of active principle.

8. The particle as claimed in claim 7, wherein the additional functional layer comprises at least one coating polymer chosen from the group consisting of cellulosic polymers and acrylic polymers, alone or as a mixture.

9. The particle as claimed in claim 1, which comprises between the core and the coating, an intermediate layer, based on a polymer chosen from the group consisting of cellulosic polymers, Acrylic polymers, povidones, copovidones, polyvinyl alcohols, alginic acids, sodium alginate, starch, pregelatinized starch, sucroses and derivatives thereof, guar gym, and polyethylene glycols, alone or as mixtures thereof.

10. A pharmaceutical or cosmetic composition comprising the coated particle of one of claims 1 to 3 or 6 to 9.

11. The composition as claimed in claim 10, which is in the form of a multiparticulate tablet which is orodispersible or dispersible.

12. A Method for producing a particle coated with active principle, a core of which consists of a first active principle and a coating with consists of a second active principle and a binding agent, comprising the following steps:

a. preparing the core consisting of the first active principle b. coating the obtained core by spraying a solution or suspension consisting of from 60-99% by weight of a second active principle and at least one binding agent, and c. drying.

13. A method for producing a particle coated with active principle, a core of which consists of a first active principle while the coating consists of a second active principle, a binding agent, and an antistatic agent, comprising the following steps:

a. preparing the core consisting of the first active principle, b. coating the obtained core by spraying a solution consisting of 60-99% by weight of a second prince that is different in nature from the first active principle, the rest up to 100% by weight of the coating consisting of at least one binding agent, and at least one antistatic agent in proportions ranging respectively up to 10% by weight relative to the coating; and c. drying.

14. The method as claimed in claim 12 or 13, wherein the step of preparing the core comprises granulometric selection of microcrystals of between 50 µm and 400 µm in size, constituting the first active principle.

15. The method as claimed in claim 12 or 13, further comprising an additional step of coating with an additional layer, the composition of which is chosen as a function of desired characteristics of taste masking and/or of release of an active principle.

16. The method as claimed in claim 12 or 13, wherein at least one binding agent is chosen from the group consisting of cellulosic polymers, Acrylic polymers, povidones, copovidones, polyvinyl alcohols, alginic acids, sodium alginate, starch, pregelatinized starch, sucroses and derivatives thereof, guar gym, and polyethylene glycols, alone or as mixtures thereof.

17. The coated particle as claimed in claim 1, wherein the coating contains from 80 to 99% by weight of the second active principle.

18. A pharmaceutical or cosmetic composition comprising the coated particle of claim 17.

19. A pharmaceutical or cosmetic composition comprising the coated particle of claim 4.

20. A pharmaceutical or cosmetic composition comprising a coated particle of claim 5.

* * * * *

UNITED STATES PATENT AND TRADEMARK OFFICE
CERTIFICATE OF CORRECTION

| | | |
|---|---|---|
| PATENT NO. | : 7,846,460 B2 | Page 1 of 1 |
| APPLICATION NO. | : 10/544311 | |
| DATED | : December 7, 2010 | |
| INVENTOR(S) | : Chenevier et al. | |

It is certified that error appears in the above-identified patent and that said Letters Patent is hereby corrected as shown below:

Claim 5, at Column 12, Line 2: Delete "gym, and polyethylene glycols, alone or as mixtures thereof." and insert --gum, and polyethylene glycols, alone or as a mixture.--

Claim 9, at Column 12, Line 27: Delete "Acrylic" and insert --acrylic--

Claim 9, at Column 12, Line 30: Delete "gym, and polyethylene glycols, alone or as mixtures thereof." and insert --gum, and polyethylene glycols, alone or as a mixture.--

Claim 12, at Column 12, Line 38: Delete "and a coating with consists" and insert --while the coating consists--

Claim 13, at Column 12, Line 53: Delete "second prince" and insert --second active principle--

Claim 16, at Column 13, Line 6: Delete "Acrylic" and insert --acrylic--

Claim 16, at Column 13, Line 9: Delete "gym, and polyethylene glycols, alone or as mixtures thereof." and insert --gum, and polyethylene glycols, alone or as a mixture.--

Signed and Sealed this
Ninth Day of August, 2011

David J. Kappos
*Director of the United States Patent and Trademark Office*